(12) United States Patent
Tamura

(10) Patent No.: US 8,771,190 B2
(45) Date of Patent: Jul. 8, 2014

(54) METHODS AND APPARATUS FOR ULTRASOUND IMAGING

(75) Inventor: Tadashi Tamura, North Haven, CT (US)

(73) Assignee: Hitachi Aloka Medical, Ltd., Tokyo (JP)

( * ) Notice: Subject to any disclaimer, the term of this patent is extended or adjusted under 35 U.S.C. 154(b) by 1173 days.

(21) Appl. No.: 11/926,206

(22) Filed: Oct. 29, 2007

(65) Prior Publication Data
US 2008/0242982 A1 Oct. 2, 2008

Related U.S. Application Data

(60) Provisional application No. 60/920,639, filed on Mar. 29, 2007.

(51) Int. Cl.
*A61B 8/00* (2006.01)
(52) U.S. Cl.
USPC ............................ 600/441; 600/437; 600/443
(58) Field of Classification Search
USPC .................................. 600/437, 438, 441, 454
See application file for complete search history.

(56) References Cited

U.S. PATENT DOCUMENTS

| | | | |
|---|---|---|---|
| 4,853,904 A | 8/1989 | Pesque | |
| 5,560,363 A * | 10/1996 | Torp et al. | 600/455 |
| 5,871,447 A | 2/1999 | Ramamurthy et al. | |
| 5,961,460 A * | 10/1999 | Guracar et al. | 600/440 |
| 6,036,643 A | 3/2000 | Criton et al. | |
| 6,322,505 B1 * | 11/2001 | Hossack et al. | 600/437 |
| 6,599,248 B1 | 7/2003 | Tamura | |
| 7,404,798 B2 | 7/2008 | Kato et al. | |
| 2002/0121993 A1 * | 9/2002 | Velazquez | 341/118 |
| 2003/0199764 A1 * | 10/2003 | Kim et al. | 600/437 |
| 2003/0236460 A1 | 12/2003 | Ma et al. | |

FOREIGN PATENT DOCUMENTS

| | | |
|---|---|---|
| JP | 11235341 A | 8/1999 |
| JP | 2001079004 A | 3/2001 |
| JP | 2002034987 | 2/2002 |

OTHER PUBLICATIONS

PCT International Search Report for PCT/JP2008/056727, dated Jun. 30, 2008.
Kenji Yoshida et al., "Japanese Office Action", dated Jan. 21, 2013, for Japanese Patent Application Serial. No. 2009-541658, 4pgs.
"Communication and Supplementary European Search Report", dated Jan. 16, 2012, for European Application No. 08739834.3-1265 / 2136713, PCT/JP2008056727, 7pgs.

* cited by examiner

*Primary Examiner* — Christopher Cook
(74) *Attorney, Agent, or Firm* — Buckley, Maschoff & Talwalker LLC

(57) ABSTRACT

Blood flow information is used to reduce noise manifest in blood vessel ultrasound B-mode images. A blood flow signal is obtained by a flow detector. After wall filtering, only the flow signal power in the blood vessel lumen remains, while signal power from stationary tissue region is suppressed. The flow signal component is used to calculate a flow component parameter that is used to generate a gain control signal α that reduces noise in a B-mode image.

10 Claims, 10 Drawing Sheets

METHODS AND APPARATUS FOR ULTRASOUND IMAGING

CROSS REFERENCE TO RELATED APPLICATIONS

This application claims the benefit of U.S. Provisional Application No. 60/920,639, filed on Mar. 29, 2007, the disclosure which is incorporated herein by reference in its entirety.

BACKGROUND OF THE INVENTION

The invention relates generally to the field of ultrasound imaging. More specifically, embodiments of the invention relate to methods and systems for reducing noise when imaging blood vessels.

Ultrasound is used to image various internal body structures such as organs like the heart and liver, blood vessels, and fetuses in pregnant women. B-mode imaging is a technique used to image blood vessels. In a vessel, blood generally exhibits lower echo power than vessel walls or surrounding tissues do, resulting in high contrast. The surface layer of vessel walls, or intima, is of particular interest in diagnosing cardiovascular diseases such as arteriosclerosis, stenosis or coronary blockages. The thickness of the intima is typically measured and is used in diagnosis. However, due to various causes, clutter noise usually appears in the lumen of blood vessels which makes the intima thickness measurement difficult.

There is a need to reduce noise present in blood vessel images.

SUMMARY OF THE INVENTION

The inventor has discovered that it would be desirable to have a system and method that uses blood flow information to reduce clutter noise in blood vessel B-mode images.

One aspect of the invention provides a method to suppress clutter noise manifest by returned ultrasound signals when imaging blood vessels by transmitting ultrasound signals to and receiving ultrasound signals from the blood vessels several times per position. The method includes processing the returned ultrasound image signals to produce a B-mode image output, demodulating the returned ultrasound signals to produce Doppler signals, wall filtering the Doppler signals to only pass the flow components of the signals, calculating a flow component parameter (e.g. amplitude a, power $a^2$, power raised to a power $a^b$ and a combination of these values), generating a gain control signal $\alpha$ based on the flow component parameter, and controlling the output of the B-mode image processor with the gain control signal $\alpha$ wherein noise manifest in the B-mode image processor output is suppressed.

Another aspect of the invention provides a method to suppress clutter noise manifest by returned ultrasound signals when imaging blood vessels by transmitting ultrasound signals to and receiving ultrasound signals from the blood vessels several times per position. Methods according to this aspect of the invention include processing the returned ultrasound image signals to produce a B-mode image output, wall filtering the returned ultrasound image signals to only pass the flow components of the signals, calculating a flow component parameter (e.g. amplitude c, power $c^2$, power raised to a power $c^b$ and a combination of these values), generating a gain control signal $\alpha$ based on the flow component parameter, and controlling the output of the B-mode image processor with the gain control signal $\alpha$ wherein noise manifest in the B-mode image processor output is suppressed.

Another aspect of the invention provides a system for suppressing clutter noise manifest by returned ultrasound signals when imaging blood vessels by transmitting ultrasound signals to and receiving ultrasound signals from the blood vessels several times per position. Systems according to this aspect of the invention include a receiver configured to receive the returned ultrasound image signals and output received signals, a B-mode image processor coupled to the receiver configured to output a B-mode processed image from the received signals, a Doppler flow detector coupled to the receiver configured to demodulate the returned ultrasound image signals to produce Doppler signals and having a wall filter configured to filter the Doppler signals and output only flow components of the Doppler signals, a gain control generator coupled to the Doppler flow detector configured to calculate a flow component parameter (e.g. amplitude a, power $a^2$, power raised to a power $a^b$ and a combination of these values)and generate a gain control signal $\alpha$ based on the flow components, and a signal combiner coupled to the gain control generator and the B-mode image processor, the signal combiner configured to modify the B-mode processed image output with the gain control signal $\alpha$ wherein noise manifest in the B-mode processed image is suppressed.

Another aspect of the invention provides a system for suppressing clutter noise manifest by returned ultrasound signals when imaging blood vessels by transmitting ultrasound signals to and receiving ultrasound signals from the blood vessels several times per position. Systems according to this aspect of the invention include a receiver configured to receive the returned ultrasound image signals and output received signals, a B-mode image processor coupled to the receiver configured to output a B-mode processed image from the received signals, an RF flow detector coupled to the receiver, the flow detector having a wall filter configured to filter the returned ultrasound RF signals and output only flow components of the received signals, a gain control generator coupled to the RF flow detector configured to calculate a flow component parameter (e.g. amplitude c, power $c^2$, power raised to a power $c^b$ and a combination of these values)and generate a gain control signal $\alpha$ based on the flow components, and a signal combiner coupled to the gain control generator and the B-mode image processor, the signal combiner configured to modify the B-mode processed image output with the gain control signal $\alpha$ wherein noise manifest in the B-mode processed image is suppressed.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
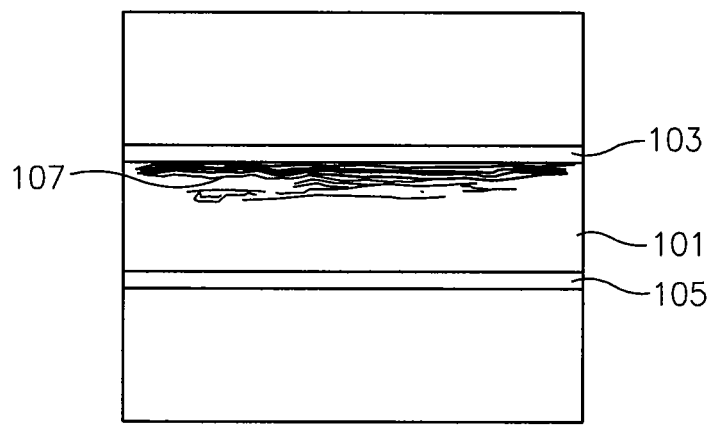
FIG. 1 is an exemplary B-mode image of a blood vessel exhibiting clutter noise.

Embodiments of the invention will be described with reference to the accompanying drawing figures wherein like numbers represent like elements throughout. Before embodiments of the invention are explained in detail, it is to be understood that the invention is not limited in its application to the details of the examples set forth in the following description or illustrated in the figures. The invention is capable of other embodiments and of being practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

It should be noted that the invention is not limited to any particular software language described or that is implied in the figures. One of ordinary skill in the art will understand that a variety of alternative software languages may be used for implementation of the invention. It should also be understood that some of the components and items are illustrated and described as if they were hardware elements, as is common practice within the art. However, one of ordinary skill in the art, and based on a reading of this detailed description, would understand that, in at least one embodiment, components in the method and system may be implemented in software or hardware.

Ultrasound is transmitted by an ultrasound transducer into a human body to image various organs, blood vessels, or a fetus in a pregnant woman. Scatterers in tissue scatter ultrasound and scattered ultrasound is returned to the transducer. A receive beamformer creates ultrasound beams and a post processor creates an image of tissues from the amplitude of the returned ultrasound signal as a B-mode image.

Blood vessels are often imaged, since they indicate cardiovascular conditions of patients. Intima thickness is often measured and used for diagnosis. However, images of intima are often obscured by noise due to various causes. Blood flow information is usually acquired using color Doppler and spectral Doppler techniques.

Color Doppler is a two-dimensional imaging technique commonly used for imaging blood flow by sending ultrasonic waves into the blood vessel and detecting the scattered ultrasound from the moving red cells. It consists of many beams similar to B-mode image. In order to detect flow velocity, color Doppler transmits ultrasound signals several times per position to detect motion. To create a two-dimensional flow image, the transmit position is shifted by sub-millimeters, or about the order of an ultrasound wavelength. The transmit position shifting is repeated about 100 times to cover several centimeters to create a two-dimensional flow image. For a phased array transducer or a sector image format, the transmit direction is changed a small angle, for example, about 0.5-1.0 degrees. This is repeated approximately 100 times to cover about 90 degrees of a sector image. For each transmit position or direction, ultrasound is transmitted several times. Received beamformed RF ultrasound signals undergo quadrature demodulation resulting in complex, Doppler I-Q signals.

The Doppler I-Q signals may contain blood flow signal components as well as stationary tissue signal components. The stationary components are typically 30-40 dB greater than the blood flow components. Therefore, it is necessary to remove the stationary signal components in order to detect blood flow accurately.

A high-pass filter is applied to the received Doppler signals from several transmits to obtain only flow signal components and is generally referred to as a wall filter because the filter removes vessel wall noise. The high-pass filter removes stationary signal components and passes only flow signal components. One form of the high-pass filter may be a signal subtraction or 2-tap FIR where the Doppler signal from a subsequent transmit is subtracted from the Doppler signal from a preceding transmit. The phase differences between the received Doppler I-Q signals from consecutive transmits indicate blood flow. Additionally, the power of the high-pass filtered Doppler I-Q signals indicates the existence of blood flow.

The system and method of the invention reduces clutter noise by decreasing B-mode signal amplitude using the above described blood flow signal. Even if clutter noise is present in a vessel lumen, blood flow is usually also present in the lumen at the same location. Clutter noise in blood vessels obscure intima and makes its thickness measurement difficult. A blood flow component parameter such as amplitude a, power $a^2$ or power raised to a power $a^b$, where b is a real number, may be calculated and used to generate a gain control signal $\alpha$ to suppress a B-mode image processor output signal at the same image position. The flow component parameters may be total or average quantities. The amount of clutter noise suppression may be in a predetermined relationship to the flow component parameter used.

Figure 2:
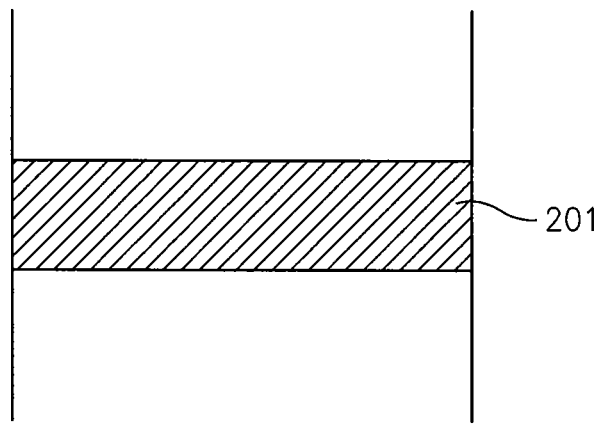
FIG. 2 is an exemplary blood flow image.
Figure 3:
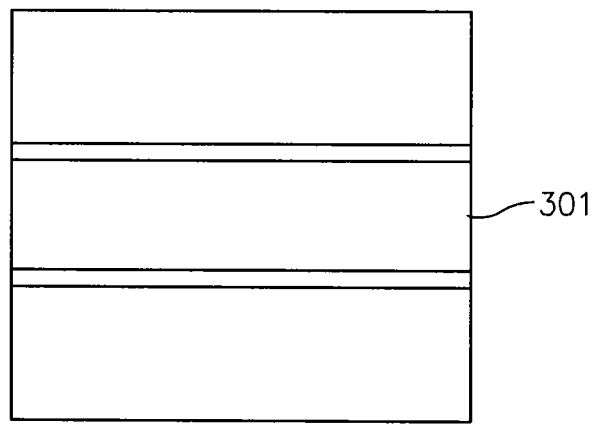
FIG. 3 is an exemplary B-mode image after clutter noise suppression.

FIG. 1 shows a blood vessel 101 image output from a typical B-mode image processor with near 103 and far 105 walls. Clutter noise 107 is shown close to the near-wall 103. FIG. 2 shows a blood flow image 201 of the same vessel which is used to decrease the gain of the B-mode image shown in FIG. 1. FIG. 3 shows a resultant image with a clean vessel lumen 301.

Figure 4:
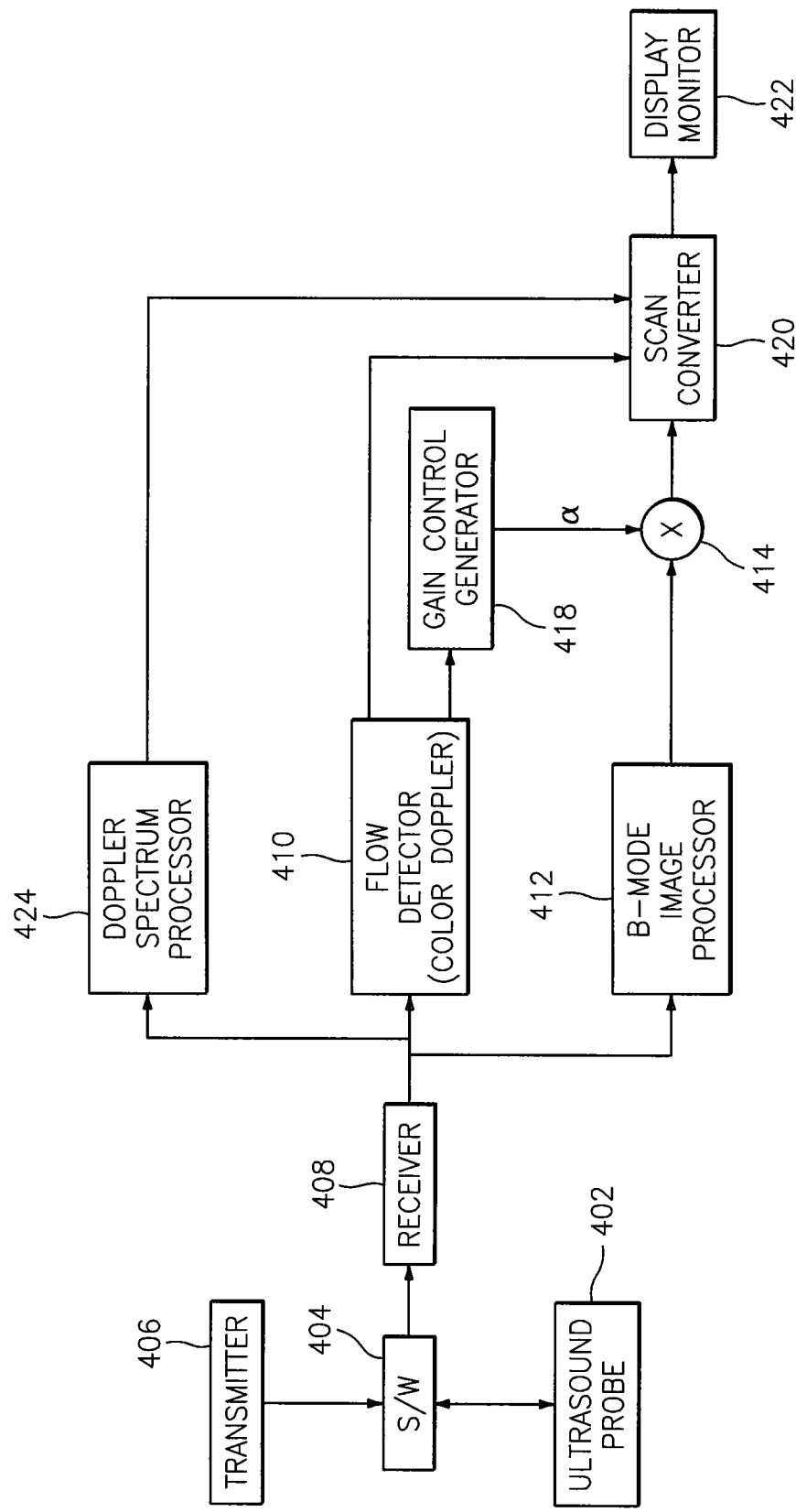
FIG. 4 is an exemplary system diagram of a clutter noise suppression system for B-mode images using Doppler flow processing.
Figure 5:
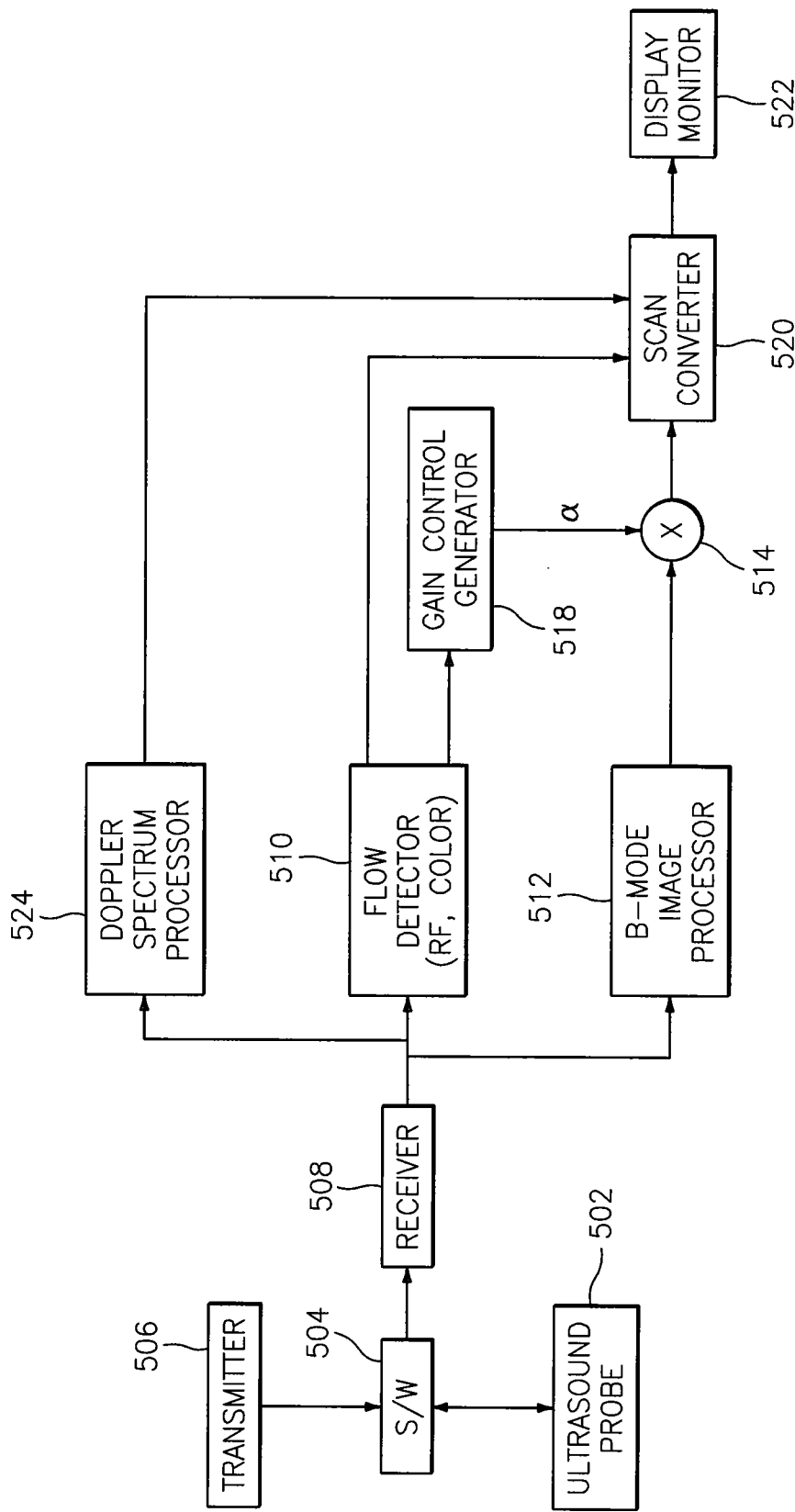
FIG. 5 is an exemplary system diagram of a clutter noise suppression system for B-mode images using RF flow processing.
Figure 14:
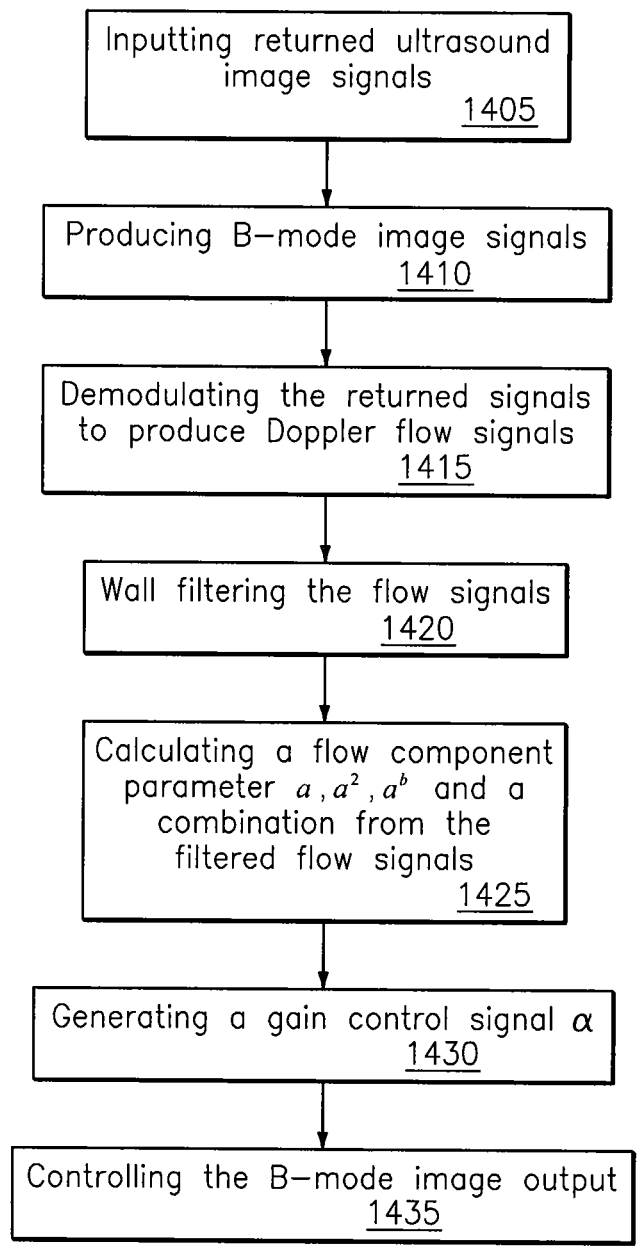
FIG. 14 is an exemplary method for B-mode image clutter noise suppression using Doppler flow processing.
Figure 15:
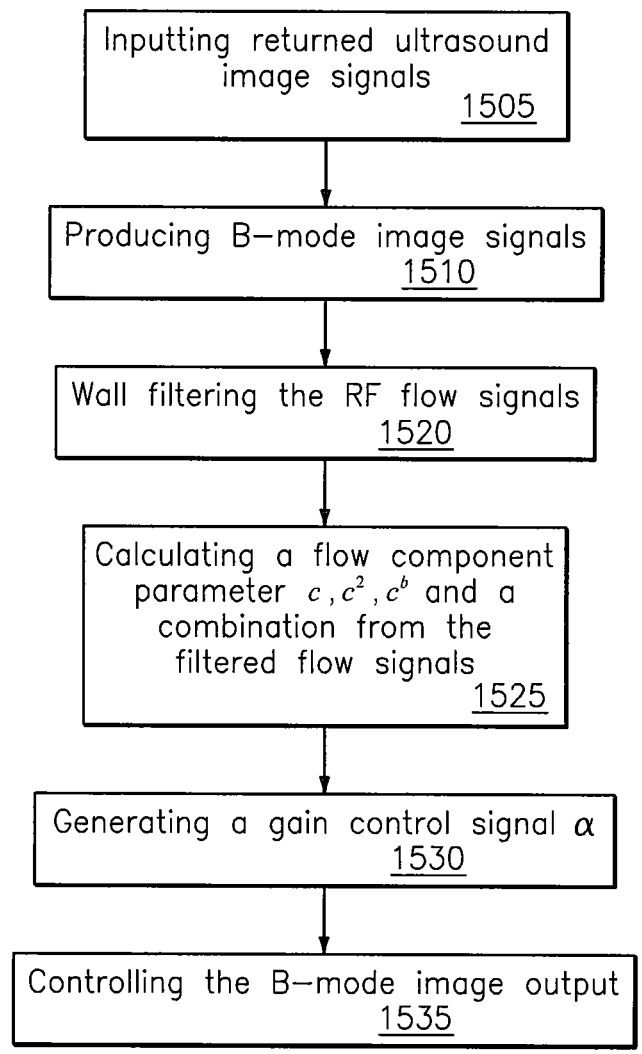
FIG. 15 is an exemplary method for B-mode image clutter noise suppression using RF flow processing.

FIG. 4 shows an ultrasound system with the invention. FIG. 14 shows a flow chart to describe the method. An ultrasound signal is transmitted from the ultrasound probe 402 driven by the transmitter 406 through the transmit/receive switch 404. The receiver 408 receives the received ultrasound signal from the probe 402 through the switch 404 and processes the signal (step 1405). The processed signal is coupled to a flow detector 410, a B-mode image processor 412 (step 1410) and a Doppler spectrum processor 424. The B-mode image processor 412 processes the received signal and outputs a B-mode image (i.e., the amplitude of the signal). The Doppler spectrum processor calculates a Doppler spectrum from the signal output by the receiver 408 and outputs the Doppler spectrum to a scan converter 420 in a Doppler spectrum mode or a combination mode with either a B-mode image and/or a color flow image.

The flow detector 410 detects blood flow, and calculates and outputs a flow component parameter which may be amplitude a, power $a^2$, power raised to a power $a^b$ or a combination of these values to the gain control signal generator 418. The gain control signal generator 418 generates a gain control signal α according to the flow component parameter and outputs the gain control signal α to a signal combiner 414 such as a multiplier or variable gain amplifier.

Figure 6:
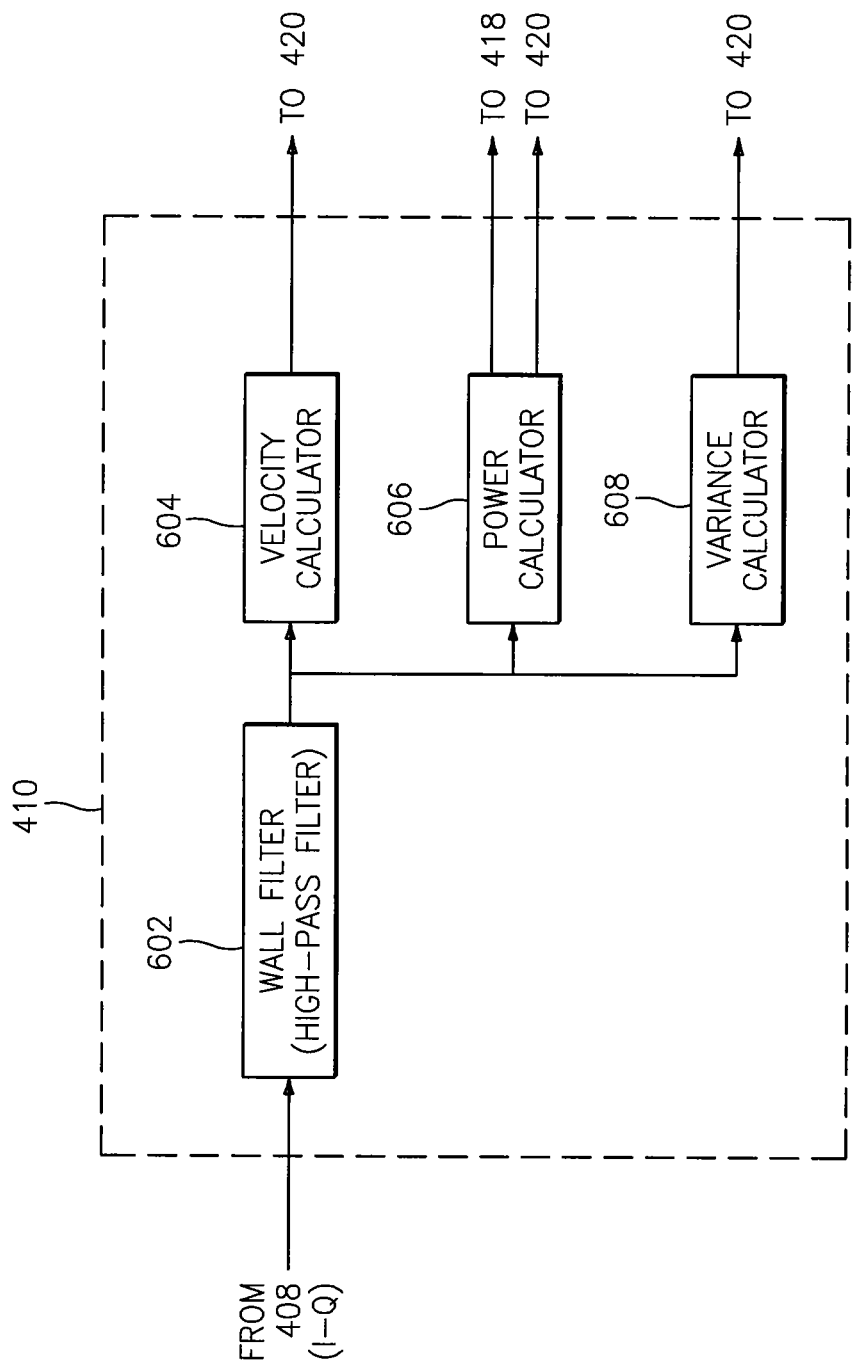
FIG. 6 is an exemplary Doppler flow detector.

FIG. 6 shows a diagram of the Doppler flow detector 410. The Doppler flow detector includes a wall filter (i.e. high-pass filter) 602, a velocity calculator 604, a power calculator 606 and a variance calculator 606. The wall filter receives the demodulated I-Q signals from the receiver 408 (step 1415). The high-pass filter cutoff or corner frequency may be user-adjustable and blocks low-frequency stationary tissue signal components passing only the higher-frequency flow signal components. The high-pass filter architecture may be an FIR (finite impulse response) filter, an IIR (infinite impulse response) filter, a polynomial filter, a regression-line filter, or other type of architecture (step 1420). The flow signal components from the wall filter 602 are coupled to the velocity calculator 604, the power calculator 606 and the variance calculator 608.

The velocity calculator 604 calculates blood flow velocity which is output to a scan converter 420 which converts the velocity signal to a scan-converted velocity image. The velocity image is then displayed on a display monitor 422 in a regular color flow mode. The variance calculator 608 calculates a variance or a turbulence indicator which is output to the scan converter 420 which converts the variance signal to a scan-converted variance image. The variance image is then displayed on the display monitor 422 in a regular color flow mode. The power calculator 606 calculates flow component parameters signal amplitude a, power $a^2$, power raised to a power $a^b$ and a combination of these values. The flow component parameters are generally calculated from the sampled high-pass filtered Doppler I-Q complex signals using $$a^2 = \sum_{i=1}^{N} z_i z_i^*, \tag{1}$$

where $z_i$ is a high-pass filtered, complex Doppler signal, i may indicate an $i^{th}$ component related to an ultrasound transmit sequence and N is the number of the high-pass filtered signal samples in discrete time. The * indicates the complex conjugate. The number of filtered outputs is usually less than the number of transmit/receive signals.

The power calculator 606 may be a DSP, an FPGA, an ASIC or discrete components such as multipliers, adders, dividers and absolute calculators.

The other flow component parameters may be obtained from the power $a^2$ by $$a = \sqrt{a^2}, \text{ or} \tag{2}$$

$$a^b = (\sqrt{a^2})^b. \tag{3}$$

Signal amplitude a and power raised to a power $a^b$ may also be obtained by $$a = \sum_{i=1}^{N} |z_i|, \text{ or} \tag{4}$$

$$a^b = \sum_{i=1}^{N} |z_i|^b. \tag{5}$$

The flow component parameters obtained by (4) and (5) are different than those derived by (2) and (3) because the order of processing steps are different (step 1425). The above flow component parameter calculations for amplitude a, power $a^2$ or power raised to a power $a^b$ represent total values. The total flow component parameters may be normalized by dividing each parameter value by the number of samples N to obtain average values at the cost of an extra calculation.

The flow component parameters amplitude a, power $a^2$, power raised to a power $a^b$ or a combination of these values are coupled to the gain control generator 418 and is used to generate a gain control signal α. To increase signal-to-noise ratio (SNR), the flow component parameters may be combined into a combined flow component parameter such as $$d_1 a + d_2 a^2 + \sum_{i} d_i a^{b(i)}$$

where $d_1$, $d_2$ and $d_i$ are real numbers that represent weighting factors and the $i^{th}$ component b(i) is also a real number. Combining more than one flow component parameter generally increases the signal-to-noise ratio and reduces noise that is uncorrelated.

$$d_1 a + d_2 a^2 + \sum_{i} d_i a^{b(i)}$$

may be calculated in the power calculator 606 and then output to the gain control generator 418 as well. The power calculator 606 may also output the power or the other values to the scan converter 420 in a color flow mode.

Figure 8:
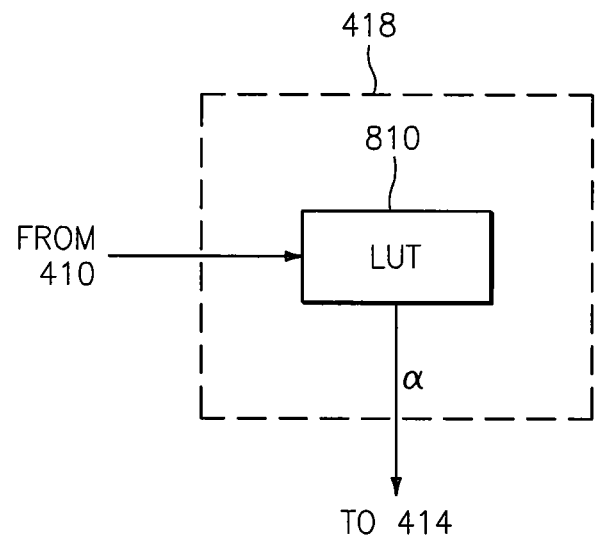
FIG. 8 is an exemplary gain control signal generator configured as a look-up table.
Figure 9:
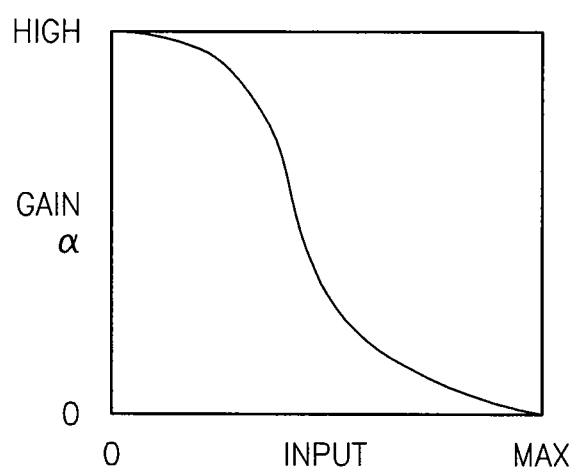
FIG. 9 is an exemplary gain control signal curve.
Figure 12:
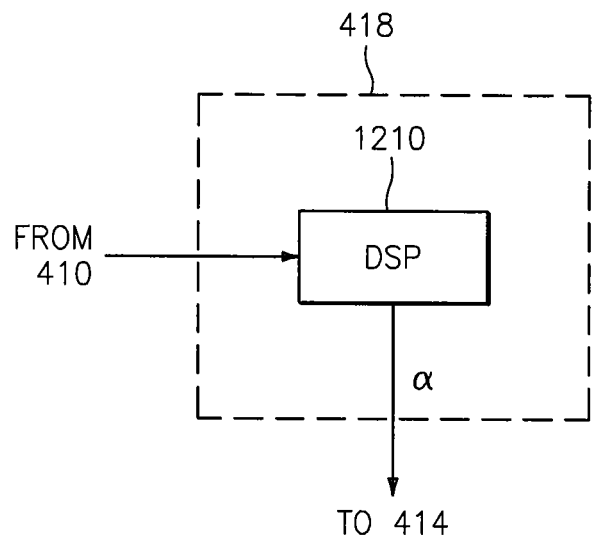
FIG. 12 is an exemplary gain control signal generator configured as a digital signal processor.

The gain control generator 418 may be, for example, a digital signal processor (DSP) 1210 as shown in FIG. 12, or a look-up table (LUT) 810 as shown in FIG. 8, or an FPGA, an ASIC or discrete components such as multipliers and adders. The gain control generator 418 uses the flow component parameters as an input. FIG. 9 shows the LUT's 810 or DSP's 1210 signal throughput as a response curve. If the input is small, the gain is high. If the input is large, the gain will be 0 or close to 0. The curve shown in FIG. 9 is exemplary. Other predetermined curves may be employed to suppress the signal output by the B-mode image processor 412 (step 1430). The gain control generator 418 gain control signal α is output and coupled to the signal combiner 414.

The B-mode image processor 412 creates and outputs a B-mode image to the signal combiner 414. The B-mode image is then output to the scan converter 420 which converts the B-mode image signal to a scan-converted image. The B-mode image is then displayed on the display monitor 422. The B-mode signal gain is controlled by the gain control signal α. For example, if the flow component parameter is large, the signal combiner's 414 gain is small, resulting in the suppression of clutter noise if present in the vessel lumen. Overall gain control removes clutter noise since blood flow exists only in the vessel lumen where clutter noise exists. If the flow component parameter is low, which may be the case in a tissue area, the signal combiner's 414 gain is large resulting in a B-mode tissue image of normal brightness. In this manner, the clutter noise, which is in the blood flow area, is reduced by the flow signal (step 1435).

In an alternate embodiment, the blood flow may be detected in the RF signal level using a cross-correlation or time-shift technique instead of using a color Doppler process. To detect flow velocity, the ultrasound signal is transmitted several times per position to detect motion. To create a two-dimensional flow image, the transmit position is shifted by sub-millimeters, or about the order of an ultrasound wavelength. The transmit position shifting is repeated about 100 times to cover several centimeters to create a two-dimensional flow image. For a phased array transducer or a sector image format, the transmit direction is changed a small angle, for example, about 0.5-1.0 degrees. This is repeated approximately 100 times to cover about 90 degrees of a sector image. For each transmit position or direction, ultrasound is transmitted several times. High-pass filtering is applied to the beamformed RF signal to remove tissue signals and pass blood flow signals. A blood flow component parameter such as amplitude c, power $c^2$, power raised to a power $c^b$, where b is a real number, or a combination of these values may be calculated and used to generate a gain control signal $\alpha$ to suppress a B-mode image processor output signal at the same position. The flow component parameters may be total or average quantities.

FIGS. 5, 7, 10, 11 and 15 show the system and method. A transmitter 506 sends ultrasound signal to the ultrasound probe 502 through a switch 504. Ultrasound is transmitted to the human subject which may include vessels. Ultrasound is then returned to the ultrasound probe 502 which converts it to an electrical signal (step 1505). The returned ultrasound signal is coupled to a receiver 508 through the switch 504. The receiver processes the signal and outputs an RF signal to an RF flow detector 510, a B-mode image processor 512 (step 1510) and a Doppler spectrum processor 524. The Doppler spectrum processor 524 processes the signal output by the receiver 508 and calculates a Doppler spectrum and outputs the Doppler spectrum to a scan converter 520 in a Doppler mode or a combination mode with either a B-mode image and/or a color flow. The B-mode image processor 512 processes the RF signal and outputs a B-mode image signal (i.e., the amplitude of the signal). The RF flow detector 510 processes the RF signal and outputs a flow component parameter amplitude c, power $c^2$, power raised to a power $c^b$ or a combination of these values to a gain control signal generator 518.

Figure 7:
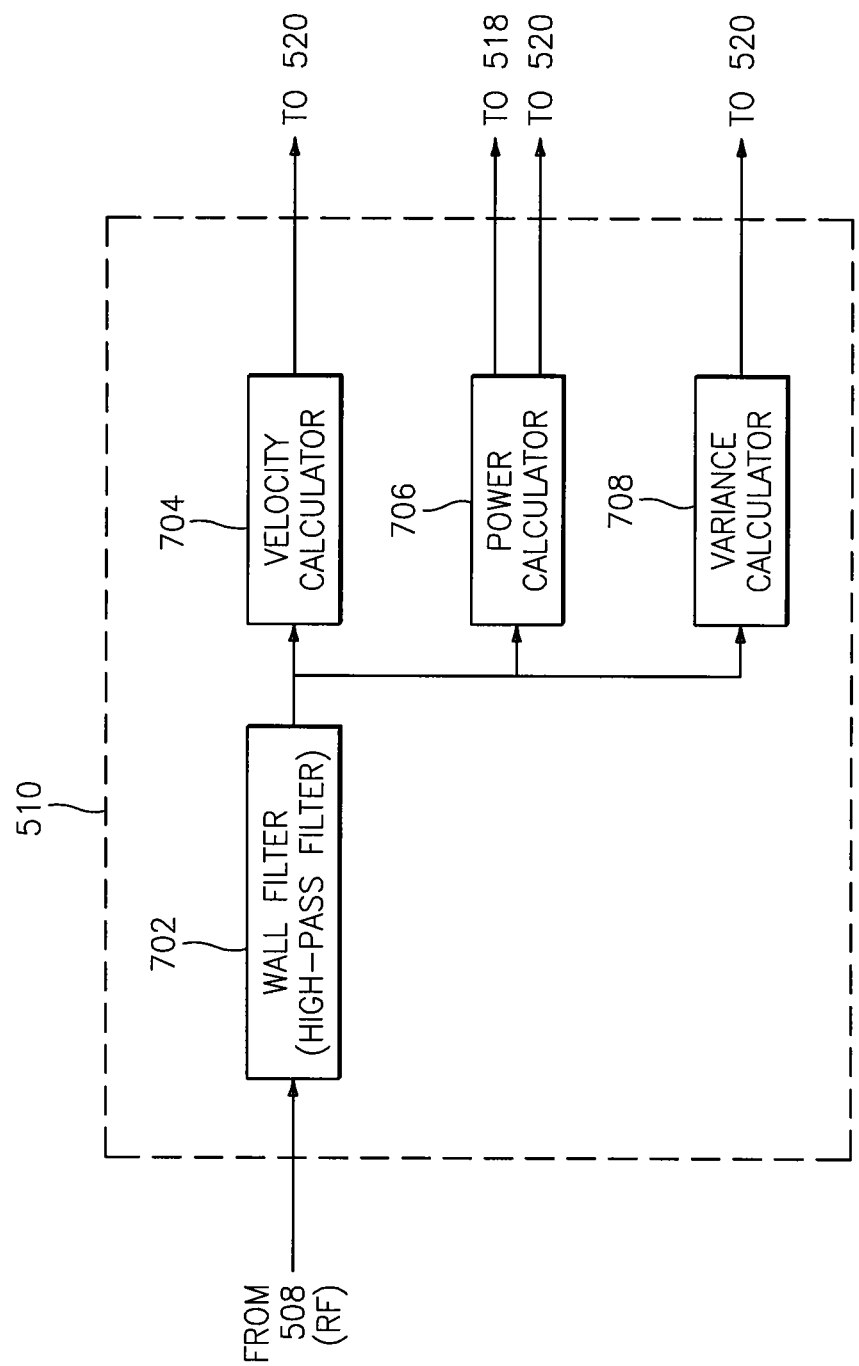
FIG. 7 is an exemplary RF flow detector.

FIG. 7 shows a diagram of the RF flow detector 510. The RF flow detector includes a wall filter (i.e., high-pass filter) 702, a velocity calculator 704, a power calculator 706 and a variance calculator 708. One form of the wall filter (i.e., high-pass filter) may be a signal subtraction or 2-tap FIR where the received RF signal from a subsequent transmit is subtracted from the RF signal from a preceding transmit. This performs high-pass filtering between two transmits. This can be extended to more transmit sequences. The high-pass filtering among several transmits removes vessel wall noise and is referred to as a wall filter. The high-pass filter may use received RF signals from two or more transmits in higher order FIR, IIR, a regression-line filter, a polynomial filter or other filter types. The high-pass filter, whose cut-off frequency may be user-adjustable and blocks low-frequency stationary tissue signal components passing only the higher-frequency flow signal components (step 1520) and is coupled to the velocity calculator 704, the power calculator 706 and the variance calculator 708.

The velocity calculator 704 calculates blood flow velocity from the wall filtered (i.e., high-pass filtered) RF signal. The velocity is output to a scan converter 520 which converts velocity signal to a scan-converted velocity image. The velocity image is then displayed on the display monitor 522 in a regular color flow mode. The variance calculator 708 calculates variance as a turbulence indicator from the wall filtered (i.e., high-pass filtered) RF signal. The variance is output to the scan converter 520 which converts the variance signal to a scan-converted variance image. The variance image is then displayed on the display monitor 522 in a regular color flow mode. The power calculator 706 calculates a flow component parameter amplitude c, power $c^2$, or power raised to a power $c^b$ from the sampled RF signals using $$c = \sum_{i=1}^{N} |x_i|, \tag{6}$$

$$c^2 = \sum_{i=1}^{N} x_i^2, \text{ and} \tag{7}$$

$$c^b = \sum_{i=1}^{N} |x_i|^b \tag{8}$$

where, $x_i$ are the high-pass filtered RF signal samples and N is the number of high-pass filtered signal samples.

The power calculator 706 may be a DSP, an FPGA, an ASIC or discrete components such as multipliers, adders, dividers and absolute calculators.

Alternately, one of these values may be calculated and the other values may be obtained from the first calculated value as follows. For example, the power $c^2$ may be first calculated, and the amplitude c and the power raised to a power $c^b$ obtained from the power $c^2$ by $$c^2 = \sum_{i=1}^{N} x_i^2, \tag{9}$$

$$c = \sqrt{c^2}, \text{ and} \tag{10}$$

$$c^b = (\sqrt{c^2})^b. \tag{11}$$

The flow component parameters calculated by (10) and (11) are different from those calculated by (6) and (8) because the order of processing steps are different (step 1525). The above flow component parameter calculations for amplitude c, power $c^2$ or power raised to a power $c^b$ represent total values. The total flow component parameters may be normalized by dividing each parameter value by the number of samples N to obtain average values at the cost of an extra calculation.

The gain control generator 518 receives the flow component parameters amplitude c, power $c^2$, power raised to a power $c^b$, or a combination of these values, and generates a gain control signal $\alpha$. To increase signal-to-noise ratio (SNR), the flow component parameters may be combined into a combined flow component parameter such as $$d_1c + d_2c^2 + \sum_i d_i c^{b(i)}$$

where $d_1$, $d_2$ and $d_i$ are real numbers that represent weighting factors and the $i^{th}$ component b(i) is also a real number. Combining more than one flow component parameter generally increases the signal-to-noise ratio and reduces noise that is uncorrelated.

$$d_1c + d_2c^2 + \sum_i d_i c^{b(i)}$$

may be calculated in the power calculator 706 and then output to the gain control generator 518 as well. The power calculator 706 may also output to the scan converter in a color flow mode.

Figure 10:
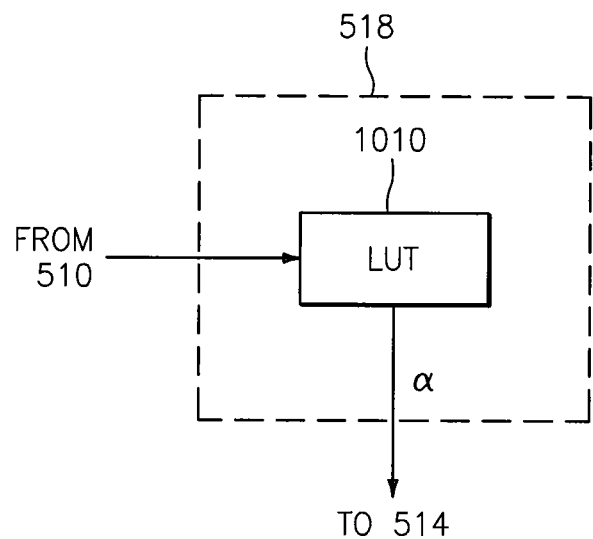
FIG. 10 is an exemplary gain control signal generator configured as a look-up table.
Figure 11:
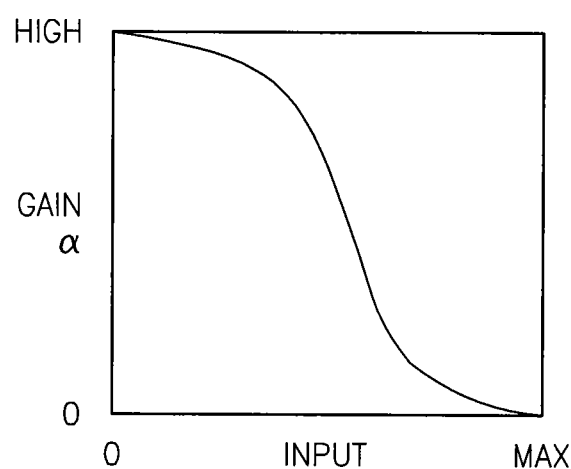
FIG. 11 is an exemplary gain control signal curve.
Figure 13:
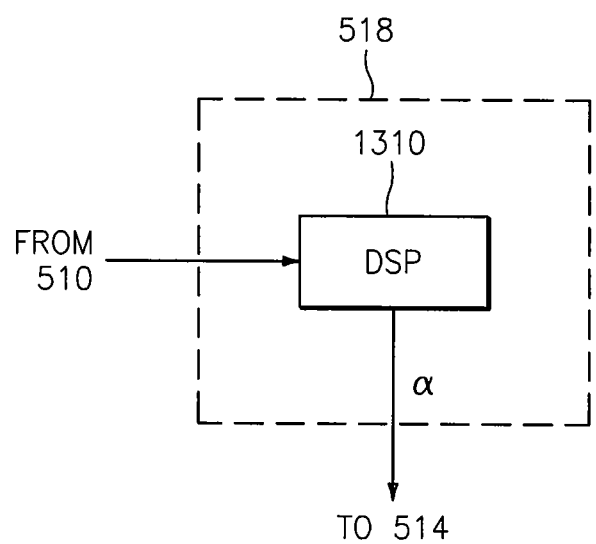
FIG. 13 is an exemplary gain control signal generator configured as a digital signal processor.

The gain control generator 518 may be a digital signal processor DSP 1310 as shown in FIG. 13 or a look-up table (LUT) 1010 as shown in FIG. 10, or an FPGA, an ASIC or discrete components such as multipliers and adders. An example response of the DSP 1310 or LUT 1010 is shown in FIG. 11. For a small value of a flow component parameter, the gain control signal α is high while a high value may yield a gain close to 0. The curve shown in FIG. 11 is exemplary. Other predetermined curves may be employed to suppress the signal output by the B-mode image processor 512 (step 1530). The gain control generator 518 gain control signal α is output and coupled to a signal combiner 514.

The signal combiner 514 may be a multiplier or variable gain amplifier. The signal combiner 514 multiplies the B-mode image with the gain control signal α and outputs a B-mode image to the scan converter 520 which converts the image signal to a scan-converted image. The image is then displayed on the display monitor 522 (step 1535).

The RF flow detection system and method may use a wide band ultrasound signal and therefore offer higher spatial resolution than the Doppler flow detection does.

One or more embodiments of the present invention have been described. Nevertheless, it will be understood that various modifications may be made without departing from the spirit and scope of the invention. Accordingly, other embodiments are within the scope of the following claims.

The invention claimed is:

1. A method for suppressing ultrasound clutter noise comprising:
   generating a B-mode image based on first ultrasound signals returned from blood vessels;
   generating Doppler signals based on second ultrasound signals returned from the blood vessels;
   determining a normalized amplitude a, a normalized power $a^2$ and a normalized power raised to a power $a^{b(i)}$, where the $i^{th}$ component b(i) is a real number, based on the Doppler signals;
   multiplying the normalized amplitude a, normalized power $a^2$ and normalized power raised to a power $a^{b(i)}$, with a corresponding weight $d_1$, $d_2$ and $d_i$, where $d_1$, $d_2$ and the $i^{th}$ component $d_i$ are real numbers;
   summing together the weighted normalized amplitude $d_1a$, normalized power $d_2a^2$ and normalized power raised to a power $d_i a^{b(i)}$ to determine a combined flow component parameter $$d_1a + d_2a^2 + \sum_i d_i a^{b(i)}$$

generating a gain control signal α based on the combined flow component parameter; and
   applying a gain to the B-mode image based on the gain control signal α to generate a second B-mode image, wherein the second B-mode image exhibits less clutter noise than the first B-mode image.

2. The method according to claim 1 further comprising:
   high-pass filtering the Doppler signals to determine the normalized amplitude a and the normalized power $a^2$.

3. The method according to claim 1 wherein the gain control signal α is a predetermined curve response based on the combined flow component parameter.

4. A method for suppressing ultrasound clutter noise comprising:
   generating a B-mode image based on first ultrasound signals returned from blood vessels;
   generating RF signals based on second ultrasound signals returned from the blood vessels;
   determining a normalized amplitude a, a normalized power $a^2$ and a normalized power raised to a power $a^{b(i)}$, where the $i^{th}$ component b(i) is a real number, based on the RF signals;
   multiplying the normalized amplitude a, normalized power $a^2$ and normalized power raised to a power $a^{b(i)}$, with a corresponding weight $d_1$, $d_2$ and $d_i$, where $d_1$, $d_2$ and the $i^{th}$ component $d_i$ are real numbers;
   summing together the weighted normalized amplitude $d_1a$, normalized power $d_2a^2$ and normalized power raised to a power $d_i a^{b(i)}$ to determine a combined flow component parameter $$d_1a + d_2a^2 + \sum_i d_i a^{b(i)}$$

generating a gain control signal α based on the combined flow component parameter; and
   applying a gain to the B-mode image based on the gain control signal αto generate a second B-mode image wherein the second B-mode image exhibits less clutter noise than the first B-mode image.

5. The method according to claim 4 further comprising:
   high-pass filtering the RF signals to determine the normalized amplitude a and the normalized power $a^2$.

6. The method according to claim 4 wherein the gain control signal α is a predetermined curve response based on the combined flow component parameter.

7. A system for suppressing ultrasound clutter noise comprising:
   a transmitter to transmit ultrasound signals to blood vessels;
   a receiver configured to receive first ultrasound image signals and second ultrasound image signals from the blood vessels;
   a B-mode image processor coupled to the receiver and configured to output a B-mode image based on the first ultrasound image signals;
   a Doppler flow detector coupled to the receiver, configured to:
      determine a normalized amplitude a, a normalized power $a^2$ and a normalized power raised to a power $a^{b(i)}$, where the $i^{th}$ component b(i) is a real number, based on the second ultrasound signals;

multiply the normalized amplitude a, normalized power $a^2$ and normalized power raised to a power $a^{b(i)}$, with a corresponding weight $d_1$ and $d_2$, where $d_1$, $d_2$ and the $i^{th}$ component $d_i$ are real numbers; and sum together the weighted normalized amplitude $d_1 a$, normalized power $d_2 a^2$ and normalized power raised to a power $d_i a^{b(i)}$ to determine a combined flow component parameter $$d_1 a + d_2 a^2 + \sum_i d_i a^{b(i)}$$

a gain control generator coupled to the Doppler flow detector and configured to generate a gain control signal α based on the combined flow component parameter; and a signal combiner coupled to the gain control generator and the B-mode image processor, the signal combiner configured to apply a gain to the B-mode image based on the gain control signal α to generate a second B-mode image wherein the second B-mode image exhibits less clutter noise than the first B-mode image.

8. The system according to claim 7 wherein the gain control signal α is a predetermined curve response based on the combined flow component parameter.

9. A system for suppressing ultrasound clutter noise comprising:

a transmitter to transmit ultrasound signals to blood vessels;

a receiver configured to receive first ultrasound image signals and second ultrasound signals from the blood vessels;

a B-mode image processor coupled to the receiver and configured to output a B-mode image based on the first ultrasound signals;

an RF flow detector coupled to the receiver, the flow detector configured to:

determine a normalized amplitude a, a normalized power $a^2$ and a normalized power raised to a power $a^{b(i)}$, where the $i^{th}$ component b(i) is a real number, based on the second ultrasound signals;

multiply the normalized amplitude a, normalized power $a^2$ and normalized power raised to a power $a^{b(i)}$, with a corresponding weight $d_1$, $d_2$ and $d_i$ where $d_i$, $d_2$ and the $i^{th}$ component $d_i$ are real numbers; and sum together the weighted normalized amplitude $d_1 a$, normalized power $d_2 a^2$ and normalized power raised to a power $d_i a^{b(i)}$ to determine a combined flow component parameter $$d_1 a + d_2 a^2 + \sum_i d_i a^{b(i)}$$

a gain control generator coupled to the RF flow detector and configured to generate a gain control signal α based on the combined flow component parameter; and a signal combiner coupled to the gain control generator and the B-mode image processor, the signal combiner configured to apply gain to the B-mode image based on the gain control signal α to generate a second B-mode image wherein the second B-mode image exhibits less clutter noise than the first B-mode image.

10. The system according to claim 9 wherein the gain control signal α is a predetermined curve response based on the combined flow component parameter.

* * * * *